United States Patent [19]
Kornfeld et al.

[11] 3,962,253
[45] June 8, 1976

[54] OXIDATION OF SELECTIVELY PROTECTED 2,3-DIHYDRO-6-METHYL-8-HYDROXY-9-ERGOLENES

[75] Inventors: Edmund C. Kornfeld; Nicholas J. Bach, both of Indianapolis, Ind.

[73] Assignee: Eli Lilly and Company, Indianapolis, Ind.

[22] Filed: Dec. 13, 1974

[21] Appl. No.: 532,332

[52] U.S. Cl............................ 260/285.5; 424/261
[51] Int. Cl.²................................. C07D 457/10
[58] Field of Search................................ 260/285.5

[56] References Cited
UNITED STATES PATENTS 2,864,822   12/1958   Fornefeld et al. ............... 260/285.5

FOREIGN PATENTS OR APPLICATIONS 517,006    9/1955   Canada........................... 260/285.5
523,783    4/1956   Canada........................... 260/285.5
1,115,726  4/1966   France........................... 260/285.5

OTHER PUBLICATIONS

Fieser et al., Reagent for Organic Chemistry, (1967) p. 642.
Rabjohn, Organic Synthesis, vol. IV, (1963) p. 582.

*Primary Examiner*—Raymond V. Rush
*Assistant Examiner*—Mary C. Vaughn
*Attorney, Agent, or Firm*—Charles W. Ashbrook; Everet F. Smith

[57] ABSTRACT

6-Methyl-8-alkanoyloxy (or 8-hydroxy)-9-ergolenes, useful as prolactin inhibitors, are prepared from 2,3-dihydro-6-methyl-8-hydroxy-9-ergolene by selective N-acylation, selective O-acylation, selective N-deacylation, and oxidation of the selectively deacylated compound.

5 Claims, No Drawings

OXIDATION OF SELECTIVELY PROTECTED 2,3-DIHYDRO-6-METHYL-8-HYDROXY-9-ERGOLENES

BACKGROUND OF THE INVENTION

The ergot alkaloids have been known for centuries and are recognized as possessing a wide variety of physiological properties. Several of the naturally occuring ergot alkaloids have been used as oxytocic agents. Recently, it has been found by Clemens, Semonsky, Meites, and their various co-workers that many ergot-related drugs, including those having either the ergoline or the 2,3-dihydro-9-ergolene ring system, are prolactin inhibitors. Certain 2,3-dihydroergolenes, available from total synthesis, have displayed decreased potency as prolactin inhibitors. It is therefore often desirous to convert such 2,3-dihydroergolenes to the corresponding unsaturated derivatives.

2,3-Dihydro-6-methyl-8-hydroxy-9-ergolene was first prepared by Kornfeld et al., as described in J. Am. Chem. Soc. 78, 3087 (1956). Oxidation of this ergolene not only removed the hydrogen atoms at the 2-and the 3-position, but additionally converted the 8-hydroxyl group to a ketone. Reduction of the ketone generally provided a mixture of epimeric 6-methyl-8-hydroxy-9-ergolenes which had to be separated into the corresponding $8\beta$-hydroxy and the $8\alpha$-hydroxy-9-ergolenes.

An object of this invention is to provide a process for converting 2,3-dihydro-6-methyl-8-hydroxy-9-ergolene to the corresponding 2,3-dehydro derivative without forming an intermediate 8-ketone. This and other objects will become apparent from the detailed description presented hereinbelow.

SUMMARY OF THE INVENTION

This invention relates to the oxidation of 2,3-dihydro-8-hydroxy-9-ergolenes and more particular to novel processes and products useful for preparing 6-methyl-8-hydroxy-9-ergolene. Still more particularly, this invention provides a process to accomplish the above objects which comprises selectively protecting and selectively deprotecting oxidizable groups in 2,3-dihydro-6-methyl-8-hydroxy-9-ergolene, first by selective acylation at the 1-position to provide a compound of the formula

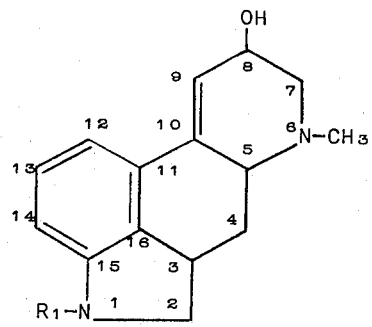

I in which $R_1$ is a halogenated acetyl group, followed by acylation of the N-acyl-protected derivative to provide a compound of the formula

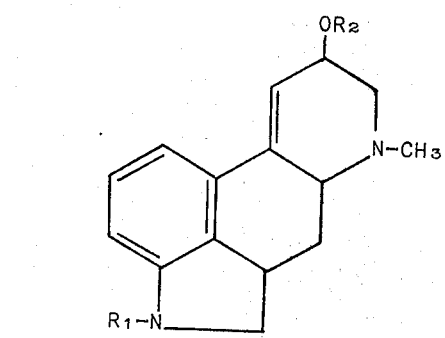

II in which $R_1$ is defined hereinabove and $R_2$ is a $C_1$-$C_4$ alkanoyl group, followed by selective cleavage of the N-acyl-protecting group ($R_1$) to provide a mono-O-protected compound of the formula

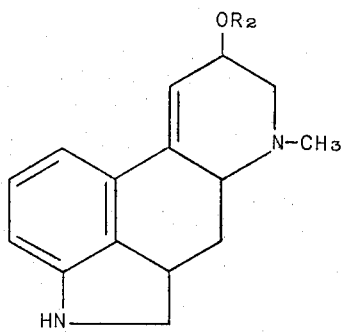

III in which $R_2$ has the above-defined meaning. 2,3-Dihydro-6-methyl-8-alkanoyloxy-9-ergolenes of the above formula can be oxidized to provide 6-methyl-8-alkanoyloxy-9-ergolenes of the formula

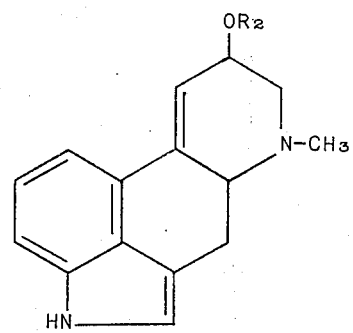

IV

Normal hydrolysis then effects cleavage of the 8-hydroxyl protecting group to provide 6-methyl-8-hydroxy-9-ergolene.

DETAILED DESCRIPTION OF THE INVENTION

As used herein, the term halogenated acetyl refers to chloroacetyl, bromoacetyl, dichloroacetyl, dibromoacetyl, iodoacetyl, and diiodoacetyl. The chloroacetyl group is an especially preferred protecting group in the present invention.

Examples of $C_1$-$C_4$ alkanoyl include groups such as the formyl, acetyl, propionyl, butyryl, and isobutyryl groups.

In accordance with the process of this invention, 2,3-dihydro-6-methyl-8-hydroxy-9-ergolene is first selectively protected at the 1-position. While any of a number of common nitrogen protecting groups can be incorporated, the halogenated acetyl groups are especially suited for protecting the indole nitrogen of the ergolene in the present invention. An especially preferred halogenated acetyl protecting group is the chloroacetyl group. The 2,3-dihydro-6-methyl-8-hydroxy-9-ergolene is generally converted to the 1-halogenated acetyl derivative by reaction with a reactive derivative of a halogenated acetic acid. Typical reactive derivatives commonly utilized include the acid halides, such as the acid chloride or acid bromide; the anhydrides; for example chloroacetic anhydride, bromoacetic anhydride, or dichloroacetic anhydride; or mixed anhydrides, such as chloroacetic-formic anhydride, and the like. Typically, the ergolene and an acylating agent, preferably chloroacetic anhydride, are commingled in approximately equimolar amounts, although a slight excess of either reactant can be used if desired. The reaction can be carried out in any of a number of unreactive solvents, including alcohols, such as methanol, ethanol, or propanol; esters such as ethyl acetate; or halogenated hydrocarbons such as chloroform or dichloromethane. While the temperature of the reaction is not critical, the reaction is normally conducted at a temperature below about 50°C., preferably in the range of 10° to 30°C. The reaction is usually complete within about 1 to 3 hours. The product can be isolated by removing the reaction solvent, for example by evaporation, and the 1-halogenoacetyl-2,3-dihydro-6-methyl-8-hydroxy-9-ergolene so formed can be further purified if desired by routine purification procedures such as chromatography, crystallization, or the like.

Reaction of a 1-halogenoacetyl-2,3-dihydro-6-methyl-8-hydroxy-9-ergolene with a $C_1$-$C_4$ alkanoyl acylating agent effects acylation of the 8-hydroxyl group. Generally the 8-hydroxyl group is protected with a group which can be removed without undue difficulty, but yet is stable to the inherent lability of the particular protecting group at the 1-position. Examples of such protecting groups include the formyl, acetyl, propionyl, and isobutyryl groups. A preferred protecting group for the 8-hydroxyl group is the acetyl group. Generally a 1-halogenoacetyl-2,3-dihydro-6-methyl-8-hydroxy-9-ergolene is treated with an acylating agent such as an acid halide, acid azide, or preferably, an acid anhydride. The acylating agent, such as acetic anhydride for example, is typically utilized in an amount sufficient to serve as reaction solvent in addition to serving as reactant. For example, the acylating agent is generally used in an amount ranging from 2 to about 300 molar excess. If desired, however, other reaction solvents such as benzene, dichloromethane, diethyl ether, or the like, can be incorporated. The acylation is normally carried out at a temperature in the range of 0° to 150°C., and is substantially complete after about 6 to 18 hours. The product can be isolated by diluting the reaction mixture with water and adjusting the pH of the resulting aqueous layer to about 8 or 9 by adding a base such as sodium carbonate or potassium bicarbonate, and extracting the N-halogenoacetyl-O-acyl product produced in the above described reaction therefrom with a water-immiscible solvent such as ethyl acetate, diethyl ether, dichlorometane, or the like. Removal of the solvent provides the desired N,O-di-protected-2,3-dihydro-6-methyl-8-hydroxy-9-ergolene, which can be further purified if desired by methods such as crystallization or chromatography.

The 1-halogenoacetyl-2,3-dihydro-6-methyl-8-alkanoyloxy-9-ergolenes thus prepared can be selectively and differentially cleaved to provide the corresponding 2,3-dihydro-6-methyl-8-alkanoyloxy-9-ergolene. The halogenated acetyl protecting groups used herein can be removed by reaction with a nucleophilic agent such as thiourea, 1-piperidinethiocarboxamide, or o-phenylenediamine. These nucleophilic reagents generally effect hdyrolysis of a halogenated acetyl protecting group by first displacing the halogen atom, and then effecting an intramolecular aminolysis, as described in detail by Masaki et al., J. Am. Chem. Soc., 90 4508 (1968), and by Steglich et al., Angew. Chem. internat. Edit., 10, 75 (1971). As hereinbefore indicated, the preferred protecting group for the 1-position of the ergolenes described herein is the chloroacetyl group, and the preferred method of removal of the chloroacetyl group is by reaction with either thiourea or 1-piperidinethiocarboxamide, most preferably with thiourea. Generally the 1-chloroacetyl-2,3-dihydro-6-methyl-8-alkanoyloxy-9-ergolene and thiourea are commingled in an unreactive solvent such as methanol, ethanol, chloroform, dichloromethane, ethyl acetate, benzene, or the like. The thiourea is normally employed in excess, for example, in an amount ranging from about a 0.1 to about a 4 molar excess relative to the ergolene derivative. The cleavage reaction is carried out at a temperature below about 150°C., for example at a temperature in the range of from 30° to 120°C. and, at this temperature, the reaction is normally complete within about 1 to 5 hours. The product can be isolated either as a free base or as an acid addition salt by the proper adjustment of the pH. For example, the reaction mixture can be diluted with water, and the resulting aqueous solution made alkaline by the addition of a base such as sodium carbonate to a pH ranging from about 8 to 9.5. The 2,3-dihydro-6-methyl-8-alkanoyloxy-9-ergolene formed in the above hydrolysis can be extracted from the aqueous alkaline reaction mixture with a suitable solvent such as diethyl ether, dichloromethane, or the like, and the solvent can be removed therefrom to provide the desired monoprotected ergolene derivative. Further purification can be accomplished if desired by standard methods such as crystallization or chromatography.

This invention also comprehends the conversion of an O-protected 2,3-dihydro-6-methyl-8-hydroxy-9-ergolene to the corresponding 6-methyl-8-alkanoyloxy-9-ergolene, and the subsequent optional hydrolysis of the alkanoyloxy group to provide 6-methyl-8-hydroxy-9-ergolene. The removal of the hydrogen atoms at the 2,3-positions of a 2,3-dihydro-6-methyl-8-alkanoyloxy-9-ergolene is generally accomplished by reaction with manganese dioxide. It will of course be understood by those skilled in organic chemistry that the desired dehydrogenation can be accomplished with any of the oxidizing agents which are similar to manganese dioxide in their oxidizing abilities. The instant oxidation is preferably accomplished, however, by commingling a 2,3-dihydro-6-methyl-8-alkanoyloxy-9-ergolene with manganese dioxide in an unreactive solvent. Typically, the manganese dioxide is employed in an amount ranging from about 0.5 to 30 molar excess; however, more or less oxidizing agent can be utilized if desired, without materially affecting the yield of the desired indole. Typical unreactive solvents commonly employed include halogenated hydrocarbons, such as chloroform or dichloromethane; esters such as ethyl acetate; ethers such as diethyl ether or dioxane; and like solvents. The oxidation is generally carried out at a temperature below about 100°C., for example at about 10° to 50° C. and, at this temperature, the reaction is substantially complete within about 30 to 90 minutes. The product can be isolated by removal of the excess manganese dioxide, for instance by filtration of the reaction mixture, followed by removal of the solvent from the filtrate, for instance by evaporation. The product so formed, a 6-methyl-8-alkanoyloxy-9-ergolene, can be further purified if desired by any of a number of routine methods including crystallization or chromatography.

As hereinbefore indicated, the 6-methyl-8-alkanoyloxy-9-ergolenes so formed are useful as prolactin inhibitors. Additionally, these compounds can be readily hydrolyzed to provide 6-methyl-8-hydroxy-9-ergolene, also useful as a prolactin inhibitor. For example, hydrolysis of an alkanoyl group, such as acetyl or propionyl for instance, can be effected by treatment of a 6-methyl-8-alkanoyloxy-9-ergolene with a base, such as aqueous sodium hydroxide or aqueous potassium hydroxide. The hydrolysis reaction is best carried out in a solvent such as methanol, ethanol, dioxane, acetone, or the like. Generally, the hydrolysis is carried out at a temperature in the range of about 10 to 50°C. and, the hydrolysis is normally complete after about 20 to 60 minutes. The product is typically isolated by extraction from the aqueous alkaline solution into a water-immiscible solvent such as chloroform or ethyl acetate. Removal of the solvent from the extracts provides 6-methyl-8-hydroxy-9-ergolene, which compound is a potent prolactin inhibitor.

While the preferred compounds described herein are those bearing an 8-alkanoyloxy or 8-hydroxy group in the $\beta$ position, the processes described hereinabove can be carried out in similar fashion on 6-methyl-8$\beta$-hydroxy-9-ergolenes. For example, 6-methyl-8$\beta$-hydroxy-9-ergolene can be converted to the 8$\alpha$-isomer by treatment with an acid such as hydrochloric acid, and subsequent selective acylations provides compounds such as 1-chloroacetyl-2,3-dihydro-6-methyl-8$\alpha$-acetoxy-9-ergolene. Removal of the chloroacetyl group and oxidation with manganese dioxide of the O-protected 2,3-dihydroergolene so formed affords 6-methyl-8$\alpha$-alkanoyloxy-9-ergolenes. The 8$\alpha$-alkanoyloxy ergolene can be hydrolyzed if desired to provide the corresponding 8$\alpha$-hydroxy ergolene. These 8$\alpha$-alkanoyloxy and 8$\alpha$-hydoxy ergolenes are useful as prolactin inhibitors and as intermediates leading to other useful ergolenes.

The following detailed examples serve to further illustrate the invention. The examples should not, however, be construed as limiting the invention to the particular aspects presented therein.

EXAMPLE 1

1-Chloroacetyl-2,3-dihydro-6-methyl-8-hydroxy-9-ergolene

A suspension of 2.25 g. of 2,3-dihydro-6-methyl-8-hydroxy-9ergolene in 200 ml. of methanol was stirred at 25°C. while 1.8 g. of chloroacetic anhydride was added portion-wise over 30 minutes. The reaction mixture was stirred at 25°C. for an additional 30 minutes, and the solvent was then removed by evaporation under reduced pressure. The reaction mixture was dissolved in 150 ml. of dichloromethane, washed with saturated aqueous sodium bicarbonate solution, dried, and the solvent was evaporated therefrom under reduced pressure, providing a white foam. The foam was crystallized from methanol to afford 1-chloroacetyl-2,3-dihydro-6-methyl-8-hydroxy-9-ergolene, M.P. 250° dec.

Analysis - Calc. for $C_{17}H_{19}ClN_2O_2$.
Theory: C, 64.05; H, 6.01; N, 8.79; Cl, 11.12.
Found: C, 63.87; H, 5.81; N, 8.62; Cl, 10.82.

EXAMPLE 2

1-Chloroacetyl-2,3-dihydro-6-methyl-8-acetoxy-9-ergolene

A mixture of 2.5 g. of 1-chloroacetyl-2,3-dihydro-6-methyl-8-hydroxy-9-ergolene in 200 ml. of acetic anhydride was heated at 100°C. for 1 hour, after which time the reaction mixture was stirred at 25°C. for 12 hours. The reaction mixture was added to 200 g. of ice and 100 ml. of water, and the pH of the aqueous mixture was adjusted to 9 by the addition of solid sodium bicarbonate. The product was extracted into chloroform from the aqueous alkaline reaction mixture, and the combined extracts were washed, dried, and the solvent was removed therefrom under reduced pressure, affording a foam. The foam was crystallized from methanol, providing 1-chloroacetyl-2,3-dihydro-6-methyl-8-acetoxy-9-ergolene, M.P. 187°–88°C.

Analysis - Calc. for $C_{19}H_{21}ClN_2O_3$.
Theory: C, 63,24; H, 5.87; N, 7.79; Cl, 9.83.
Found: C, 62.23; H, 5.86; N, 8.02; Cl, 9.60.

EXAMPLE 3

2,3-Dihydro-6-methyl-8-acetoxy-9-ergolene

A solution of 1.7 g. of 1-chloroacetyl-2,3-dihydro-6-methyl-8-acetoxy-9-ergolene in 100 ml. of ethyl alcohol containing 1.0 g. of thiourea was heated at reflux under a nitrogen atmosphere for 2 hours. The reaction mixture was cooled to 25°C.; 100 ml. of water was added, and the pH was adjusted to 9.0 by the addition of sodium bicarbonate. The alkaline aqueous solution was extracted with chloroform. The combined chloroform extracts were dried, and the solvent was removed under reduced pressure providing a white foam. Crystallization of the foam from diethyl ether afforded 2,3-dihydro-6-methyl-8-acetoxy -9-ergolene, M.P. 178°–181°C.

Analysis - Calc. for $C_{17}H_{20}N_2O_2$.
Theory: C, 71.80; H, 7.09; N, 9.85.
Found: C, 71.75; H, 7.24; N, 9.68.

EXAMPLE 4

6-methyl-8-acetoxy-9-ergolene

A solution of 4.4 g. of 2,3-dihydro-6-methyl-8-acetoxy-9-ergolene in 250 ml. of chloroform was stirred at 25°C. while 30 g. of manganese dioxide was added in one portion. The reaction mixture was stirred for 45 minutes and then filtered. The filtrate was concentrated to 50 ml. under reduced pressure, and then filtered through 10 g. of florisil. Removal of the solvent from the filtrate provided a red oil which crystallized from diethyl ether, affording 6-methyl-8-acetoxy-9-ergolene, M.P. 151°–152°C.

Analysis - Calc. for $C_{17}H_{18}N_2O_2$.
Theory: C, 72.32; H, 6.43; N, 9.92.
Found: C, 72.11; H, 6.59; N, 9.82.

EXAMPLE 5

6-methyl-8-hydroxy-9-ergolene

A solution of 925 mg. of 6-methyl-8-acetoxy-9-ergolene in 50 ml. of ethanol was stirred at 25°C. under a nitrogen atmosphere while 25 ml. of 20 percent aqueous potassium hydroxides was added in one portion. The reaction mixture was stirred for 30 minutes at 25°C. After adding 100 ml. of water to the reaction mixture, the product was extracted therefrom with chloroform. The chloroform extracts were combined, dried, and the solvent was removed therefrom under reduced pressure to provide the product as a foam. The foam was crystallized from benzene, affording 6-methyl-8-hydroxy-9-ergolene, M.P. 212°–215°C.

EXAMPLE 6

2,3-Dihydro-6-methyl-8α-hydroxy-9-ergolene

A solution of 5.9 g. of 2,3-dihydro-6-methyl-8β-hydroxy-9-ergolene in 200 ml. of concentrated hydrochloric acid was stirred at 25°C. for 17 hours. The reaction mixture was concentrated to 100 ml. under reduced pressure, and then diluted by adding 100 ml. of water. The reaction mixture was made alkaline by adding potassium hydroxide to adjust the pH to 11. The product was extracted from the aqueous alkaline solution with chloroform. The chloroform extracts were combined, washed with water, dried, and the solvent was removed therefrom under reduced pressure, providing a foam. The foam was crystallized from ethyl acetate to afford 2,3-dihydro-6-methyl-8α-hydroxy-9-ergolene, M.P. 221°C. dec.

EXAMPLE 7

Following the procedure set forth in Example 1 above, 2,3-dihydro-6-methyl-8α-hydroxy-9ergolene was acylated with chloroacetic anhydride to provide 1-chloroacetyl-2,3-dihydro-6-methyl-8α-hydroxy-9-ergolene, M.P. 250°C. dec.

Analysis - Calc. for $C_{17}H_{19}ClN_2O_2$.
Theory: C, 64.05; H, 6.01; N, 8.79; Cl, 11.12.
Found: C, 63.76; H, 6.19; N, 8.86; Cl, 11.39.

EXAMPLE 8

Following the procedure of Example 2 above, 1-chloroacetyl-2,3-dihydro-6-methyl-8α-hydroxy-9-ergolene was acylated with acetic anhydride to afford 1-chloroacetyl-2,3-dihydro-6-methyl-8α-acetoxy-9-ergolene, M.P. 200°C. dec.

Analysis - Calc. for $C_{19}H_{21}N_2O_3$.
Theory: C, 63.24; H, 5.87; N, 7.76; Cl, 9.83.
Found: C, 63.36; H, 5.98; N, 7.96; Cl, 9.85.

EXAMPLE 9

Following the procedure of Example 3 above, 1-chloroacetyl-2,3-dihydro-6-methyl-8α-acetoxy-9-ergolene was reacted with thiourea to provide 2,3-dihydro-6-methyl-8α-acetoxy-9-ergolene, M.P. 153°–155°C.

EXAMPLE 10

Following the procedure set forth in Example 4 above, 2,3-dihydro-6-methyl-8α-acetoxy-9-ergolene was reacted with manganese dioxide to provide 6-methyl-8α-acetoxy-9-ergolene, M.P. 160°C. dec.

We claim:
1. A compound of the formula

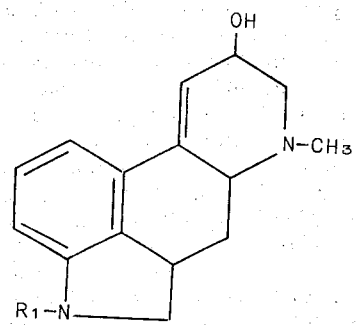

wherein:
$R_1$ is a halogenated acetyl group selected from the group consisting of chloroacetyl, bromoacetyl, iodoacetyl, dichloroacetyl, dibromoacetyl, and diiodoacetyl.

2. The compound of claim 1 wherein $R_1$ is chloroacetyl.

3. A compound of the formula

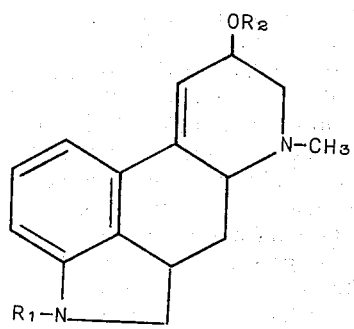

wherein:
$R_1$ is a halogenated acetyl group selected from the group consisting of chloroacetyl, bromoacetyl, iodoacetyl, dichloroacetyl, dibromoacetyl, and diiodoacetyl; and
$R_2$ is $C_1$-$C_4$ alkanoyl.

4. The compound of claim 3 wherein $R_1$ is chloroacetyl and $R_2$ is acetyl.

5. The process for converting 2,3-dihydro-6-methyl-8-hydroxy-9-ergolene to 6-methyl-8-hydroxy-9-ergolene comprising the steps of
A. selectively reacting 2,3-dihydro-6-methyl-8-hydroxy-9-ergolene with chloroacetic anhydride to obtain 1-chloroacetyl-2,3-dihydro-6-methyl-8-hydroxy-9-ergolene;
B. reacting 1-chloroacetyl-2,3-dihydro-6-methyl-8-hydroxy-9-ergolene with a $C_1$-$C_4$ alkanoyl acylating agent to obtain a 1-chloroacetyl-2,3-dihydro-6-methyl-8-($C_1$-$C_4$ alkanoyloxy)-9-ergolene;
C. selectively hydrolyzing said 1-chloroacetyl-2,3-dihydro-6-methyl-8-($C_1$-$C_4$-alkanoyloxy)-9-ergolene with thiourea to obtain 2,3-dihydro-6-methyl-8-($C_1$-$C_4$-alkanoyloxy)-9 -ergolene;
D. oxidizing the 2,3-dihydro-6-methyl-8-($C_1$-$C_4$-alkanoyloxy)-9-ergolene thus formed with manganese dioxide to yield a 6-methyl-8-($C_1$-$C_4$-alkanoyloxy)-9-ergolene; and
E. hydrolyzing said 6-methyl-8-($C_1$-$C_4$-alkanoyloxy)-9-ergolene with an alkali metal hydroxide to obtain 6-methyl-8-hydroxy-9-ergolene.

* * * * *